US010485446B2

(12) United States Patent
Everling et al.

(10) Patent No.: US 10,485,446 B2
(45) Date of Patent: Nov. 26, 2019

(54) ELECTROPHYSIOLOGICAL MAPPING SYSTEM USING EXTERNAL ELECTRODES

(71) Applicant: St. Jude Medical, Atrial Fibrillation Division, Inc., St. Paul, MN (US)

(72) Inventors: Bruce R. Everling, Eagan, MN (US); Eric J. Voth, Maplewood, MN (US)

(73) Assignee: St. Jude Medical, Atrial Fibrillation Division Inc., St. Paul, MN (US)

(*) Notice: Subject to any disclaimer, the term of this patent is extended or adjusted under 35 U.S.C. 154(b) by 716 days.

(21) Appl. No.: 15/135,767

(22) Filed: Apr. 22, 2016

(65) Prior Publication Data

US 2016/0310039 A1 Oct. 27, 2016

Related U.S. Application Data

(63) Continuation of application No. 13/995,421, filed as application No. PCT/US2011/051503 on Sep. 14, 2011, now Pat. No. 9,345,405.

(Continued)

(51) Int. Cl.
*A61B 5/053* (2006.01)
*A61B 5/00* (2006.01)
*A61B 5/0402* (2006.01)
*A61B 5/055* (2006.01)
*A61B 6/03* (2006.01)
(Continued)

(52) U.S. Cl.
CPC .......... *A61B 5/0536* (2013.01); *A61B 5/0035* (2013.01); *A61B 5/0044* (2013.01); *A61B 5/0402* (2013.01); *A61B 5/055* (2013.01); *A61B 5/6805* (2013.01); *A61B 5/7225* (2013.01); *A61B 5/742* (2013.01); *A61B 5/7475* (2013.01); *A61B 6/032* (2013.01); *A61B 6/461* (2013.01); *A61B 6/467* (2013.01); *A61B 6/504* (2013.01);
(Continued)

(58) Field of Classification Search
CPC ..... A61B 5/004; A61B 5/0044; A61B 5/0035; A61B 5/0402; A61B 5/0536; A61B 2017/00026
USPC ....................................................... 600/547
See application file for complete search history.

(56) References Cited

U.S. PATENT DOCUMENTS 4,961,428 A 10/1990 Nikias et al.
6,055,452 A 4/2000 Pearlman
(Continued)

FOREIGN PATENT DOCUMENTS

EP 1897490 3/2008
WO 1999/005963 7/1998

*Primary Examiner* — Adam J Eiseman
(74) *Attorney, Agent, or Firm* — Dykema Gossett PLLC

(57) ABSTRACT

A system and method for generating an electrophysiological map are provided. The system includes an electronic control unit (ECU) configured to receive a signal generated by an electrode disposed at a position on an external surface of the body and indicative of electric potential. The ECU is further configured to identify a surface boundary of an object of interest within the body using an image of the object. The ECU is further configured to identify intervening objects along a pathway between the position on the external surface and the surface boundary of the object of interest from one or more images of the pathway. The ECU is further configured to obtain an impedance value for each of the intervening objects and to determine an electric potential at the surface boundary of the object of interest responsive to the signal from the electrode and the impedance values of the intervening objects.

20 Claims, 3 Drawing Sheets

Related U.S. Application Data

(60) Provisional application No. 61/428,596, filed on Dec. 30, 2010.

(51) Int. Cl.
*A61B 5/0408* (2006.01)
*G06K 9/00* (2006.01)
*A61B 6/00* (2006.01)

(52) U.S. Cl.
CPC ........ *G06K 9/0057* (2013.01); *A61B 5/04085* (2013.01); *G06K 2209/051* (2013.01)

(56) References Cited

U.S. PATENT DOCUMENTS

| | | |
|---|---|---|
| 7,016,719 B2 | 3/2006 | Rudy et al. |
| 7,774,051 B2 | 8/2010 | Voth |
| 2006/0085049 A1 | 4/2006 | Cory et al. |
| 2008/0177192 A1 | 7/2008 | Chen et al. |
| 2009/0053102 A2 | 2/2009 | Rudy |
| 2010/0191131 A1 | 7/2010 | Revishvili |
| 2010/0275921 A1 | 11/2010 | Schindhelm |
| 2012/0035459 A1 | 2/2012 | Revishvili |

ELECTROPHYSIOLOGICAL MAPPING SYSTEM USING EXTERNAL ELECTRODES

CROSS-REFERENCE TO RELATED APPLICATIONS

This application is a continuation of U.S. application Ser. No. 13/995,421, filed 18 Jun. 2013 (the '421 application), now U.S. Pat. No. 9,345,405, which is a national stage application of International application no. PCT/US2011/051503, filed 14 Sep. 2011 (the '503 application), which in turn claims the benefit of and priority to U.S. application No. 61/428,596, filed 30 Dec. 2010 (the '596 application). The '421 application, '503 application and '596 application are each hereby incorporated by reference as though fully set forth herein.

BACKGROUND OF THE INVENTION a. Field of the Invention

This invention relates to a system and method for generating an electrophysiological map of an object of interest within the body such as the heart. In particular, the invention relates to a system and method that enable derivation of the map without inserting an EP mapping catheter into the body by using electrodes that are placed on an external surface of the body.

b. Background Art

The use of electrophysiological (EP) mapping data in the diagnosis and treatment of tissues within a body is well known. For example, EP maps of heart tissue can be used to guide ablation catheters which are used to convey an electrical stimulus to a region of interest within the heart and create tissue necrosis. Ablation catheters may be used to create necrosis in heart tissue to correct conditions such as atrial arrhythmia (including, but not limited to, ectopic atrial tachycardia, atrial fibrillation, and atrial flutter). Arrhythmias can create a variety of dangerous conditions including irregular heart rates, loss of synchronous atrioventricular contractions and stasis of blood flow which can lead to a variety of ailments and even death. It is believed that the primary cause of arrhythmia is stray electrical signals within the left or right atrium of the heart. The ablation catheter imparts ablative energy (e.g., radiofrequency energy) to the heart tissue to create a lesion in the heart tissue. This lesion disrupts electrical pathways and thereby limits or prevents stray electrical signals that lead to arrhythmia. In addition to guiding ablation catheters, EP maps can also be used to evaluate the effectiveness of ablation therapy.

In a conventional EP mapping system, a catheter is inserted within a vessel located near the surface of a body (e.g., in an artery or vein in the leg, neck, or arm) and maneuvered to a region of interest within the body. Electrodes disposed at one end of the catheter detect changes in electrical potential resulting from the transmission of electrical signals between points on the body. In the EP mapping system sold under the registered trademark "ENSITE" by the assignee of the present invention, St. Jude Medical, Atrial Fibrillation Division, Inc., surface electrode patches are applied in several locations on a body. Electrical signals are transmitted between the patches along orthogonal pathways and one or more electrodes supported on a catheter disposed within the body detect changes in voltage and generate signals that are used to generate an image of a tissue surface Although existing EP mapping systems function well for their intended purpose, it is desirable to reduce or eliminate the need to insert an EP mapping catheter within the body to obtain EP data. Inserting an EP mapping catheter into the body creates a variety of risks including, for example, potential damage to internal tissues and adverse patient reactions to anesthesia used during the EP mapping procedure. In addition, as with any surgical procedure, insertion of an EP mapping catheter requires significant time and resources on the part of the patient and/or clinician in preparing for the procedure, carrying out the procedure, and in recovery. Furthermore, inserting an EP mapping catheter may cause patient discomfort during and/or following the procedure.

In order to address the issues set forth above, approaches have been developed to obtain EP data for internal body structures such as the heart using electrodes placed on an external body surface. In U.S. Pat. No. 7,016,719, for example, an electrode vest is placed over the patient. An image of the heart such as a fluoroscopic, ultrasound, computed tomography (CT), or magnetic resonance (MR) image is used to define a geometric relationship between the electrodes on the external body surface and the heart. Using this relationship, electrical potentials on the heart surface are then determined in response to potentials measured by the external electrodes. Although the system described in U.S. Pat. No. 7,016,719 eliminates the need for an EP mapping catheter, the accuracy of the system is limited. In particular, the geometric relationship established by the system fails to account for the wide variety of tissues types disposed between the external surface of the body and the heart surface. Different types of tissues within the body have significantly varying impedances. Further, the amount of these tissues will vary along any given pathway from the external body surface to the heart. The geometric relationships advanced in the system described in U.S. Pat. No. 7,016,719 cannot account for this variation in tissue types and amounts.

The inventors herein have recognized a need for a system and method for generating an electrophysiological map that will minimize and/or eliminate one or more of the above-identified deficiencies.

BRIEF SUMMARY OF THE INVENTION

It is desirable to provide a system and method for generating an electrophysiological map. In particular, it is desirable to provide a system and method that will enable generation of the map without the need to insert an EP mapping catheter into the body.

A system for generating an electrophysiological map in accordance with one embodiment of the invention includes an electrode disposed at a position on an external surface of a body. The system further includes an electronic control unit electrically connected to the electrode. The electronic control unit is configured to receive a signal generated by the electrode. The signal is indicative of an electric potential measured at the position on the external surface of the body. The electronic control unit is further configured to identify a surface boundary of an object of interest within the body using an image (or model) of the object of interest. The electronic control unit is further configured to obtain an impedance value for one or more intervening objects along a pathway between the position on the external surface of the body and the surface boundary of the object of interest. The electronic control unit is further configured to determine an electric potential at the surface boundary of the object of interest responsive to the signal from the electrode and the impedance value of the intervening object along the pathway.

A method for generating an electrophysiological map in accordance with one embodiment of the present invention includes the step of receiving a signal generated by an electrode disposed at a position on an external surface of a body. The signal is indicative of an electric potential measured at the position. The method further includes the step of identifying a surface boundary of an object of interest in the body using an image (or model) of the object of interest. The method further includes the step of obtaining impedance values for one or more intervening objects along a first pathway between the position on the external surface of the body and the surface boundary of the object of interest. The method further includes the step of determining an electric potential at the surface boundary of the object of interest responsive to the signal from the electrode and the impedance values of the intervening objects along the pathway.

A system and method in accordance with the above-described embodiments of the present invention are advantageous because they generate much more accurate electrophysiological maps of the heart and other internal body structures. In particular, the system and method identify different objects disposed between the heart and body surface and account for the varying impedances created by these objects. As a result, the electric potentials measured by the electrodes at the external body surface can be adjusted to account for the different objects and amounts of these objects along individual pathways and a more accurate reading of the electrical activity in the heart can be obtained.

The foregoing and other aspects, features, details, utilities and advantages of the present invention will be apparent from reading the following description and claims, and from reviewing the accompanying drawings.

DETAILED DESCRIPTION OF EMBODIMENTS OF THE INVENTION

Figure 1:
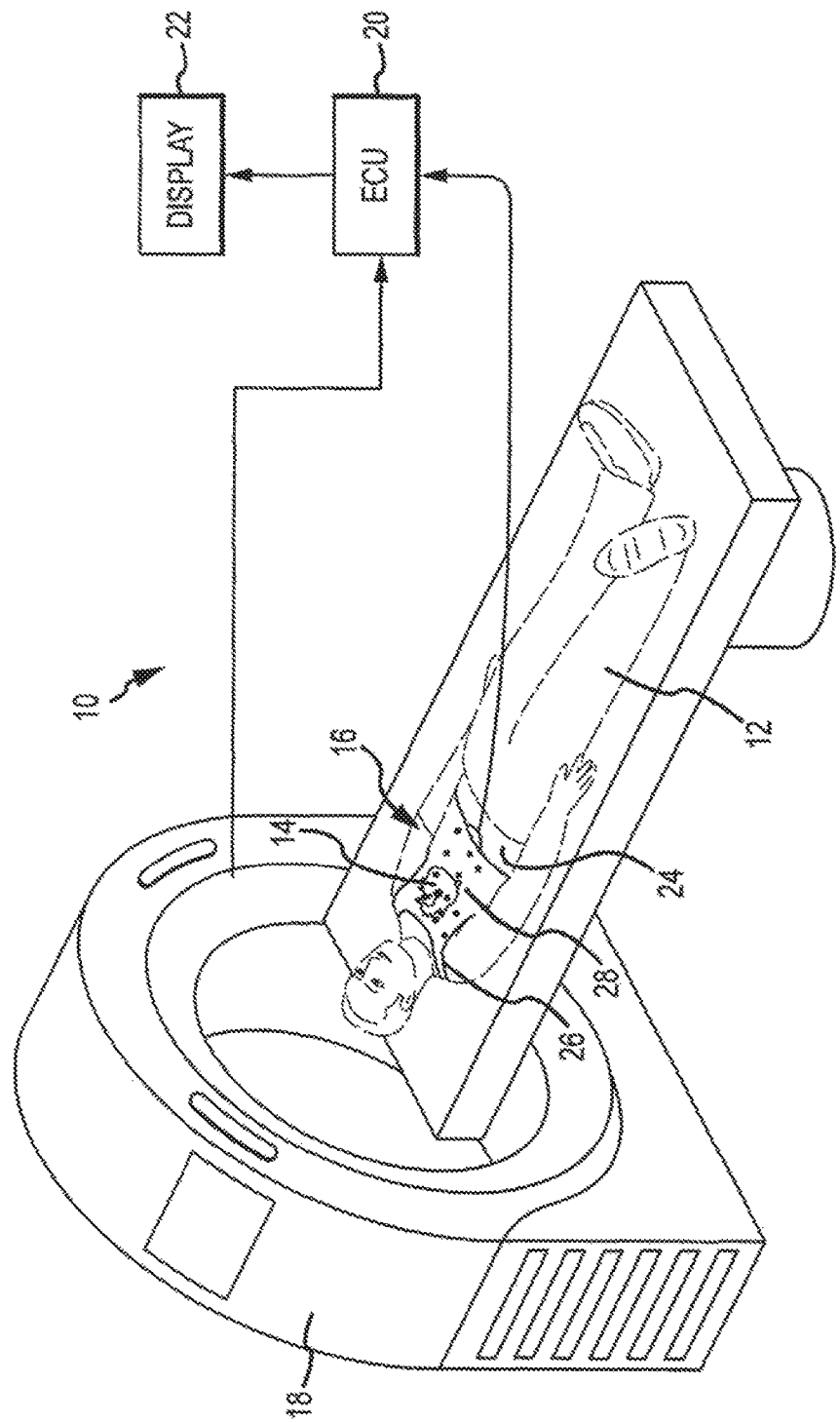
FIG. 1 is a diagrammatic view of a system in accordance with one embodiment of the present teachings.

Referring now to the drawings wherein like reference numerals are used to identify identical components in the various views, FIG. 1 illustrates one embodiment of a system 10 for generating an electrophysiological (EP) map of an object of interest in a body 12 such as a heart 14. Although the object of interest is a heart 12 in the illustrated embodiment, it should be understood that the system and method disclosed herein could be applied to other objects within body 12 including, for example, a brain. Further, although body 12 is illustrated as a human body, it should be understood that the system and method disclosed herein could be applied to animal bodies as well. System 10 may include an electrode assembly 16, an imaging system 18 and an electronic control unit (ECU) 20 and a display 22.

Electrode assembly 16 is provided to detect electrical impedances at positions on the external surface 24 of body 12. Assembly 16 may include a housing 26 and a plurality of electrodes 28.

Housing 26 is provided to position electrodes 28 at predetermined positions relative to each other and relative to body 12. Housing 26 is preferably made from a relatively flexible material such that housing 26 can be properly arranged on, or worn by, the patient. In particular, housing 26 may include a fixed number of electrodes 28 mounted within a semi-elastic material that may be stretched across body 12 to allow the electrodes 28 to be evenly distributed across body 12. When worn, housing 26 may wrap around body 12 to substantially or completely surround the torso to enable electric potential and electrogram readings from substantially all sides of the torso. Housing 26 may include insulated conductors extending therethrough between electrodes 28 and one or more connectors through which electrodes 28 may be coupled to directly to ECU 20 or indirectly to ECU 20 through signal processing circuitry including conventional amplifiers, filters, and analog to digital converters. It should be understood, however, that housing 26 may alternatively include such signal processing circuitry within housing 26.

Electrodes 28 are provided to detect electric potentials on surface 24 of body 12. Electrodes 28 are conventional in the art and may be similar in construction to surface ECG electrodes. Electrodes 28 are preferably arranged in a predetermined position on surface 24 by positioning of housing 26. In particular, electrodes 28 are preferably arranged to align with estimates of the electrode positions in the software model implemented on ECU 20. Alternatively, the actual electrode positions may be input by an operator or calibrated prior to operation. Surface 24 may be marked with ink in a conventional manner to insure registration of the position of electrodes 28 relative to surface 24 during a procedure and/or across multiple procedures.

Imaging system 18 is provided to capture images (including models)) of the object of interest in body 12 such as heart 14. System 18 may also be provided to capture images (including models) of intervening objects between the object of interest and surface 24 of body 12. Intervening objects may include, for example, connective tissues such as that found in bone, fat, blood and lymph nodes, epithelial tissues, muscle tissues and nerve tissues or fluids such as blood, pericardial fluid or saline. Imaging system 18 may comprise a computed tomography (CT) imaging system, a magnetic resonance (MR) imaging system, a three-dimensional rotational angiography (3DRA) system or an electrical impedance tomography system (EIT). In the case of a CT system, imaging system 18 scans body 12 in a conventional manner from various angles and derives a number indicative of the density of the intervening object in a given location (and, therefore, the type of object). In the resulting image, the color and/or intensity in a given pixel correlates to the object's density at that location. Because the intensity of each pixel is indicative of the object's density and type and because impedance values for various tissue types can be derived, the information contained in the images can be used to determine the impedance at the location shown in the image. As discussed below, the images captured by imaging system 18 may be registered in the coordinate system of the electrodes 28. In one embodiment of the invention, registration is accomplished by placing fiducial markers on surface 24 of body 12 corresponding to the location of one or more electrodes 28. The markers may, for example, be disposed within a housing similar to housing 26 and correspond to certain electrodes 28. The housing and markers are placed on surface 24 of body 12 prior to image capture by imaging system 18.

ECU 20 provides a means for controlling the operation of various components of system 10 including display 22. ECU 20 also provides a means for generating an electrophysiological map of the object of interest such as heart 14. ECU 20 may comprise a programmable microprocessor or microcontroller or may comprise an application specific integrated circuit (ASIC). ECU 20 may include a central processing unit (CPU) and an input/output (I/O) interface through which ECU 20 may receive a plurality of input signals including signals generated by electrodes 28 and imaging system 18 and generate a plurality of output signals including those used to control and/or provide data to display 22.

Figure 2:
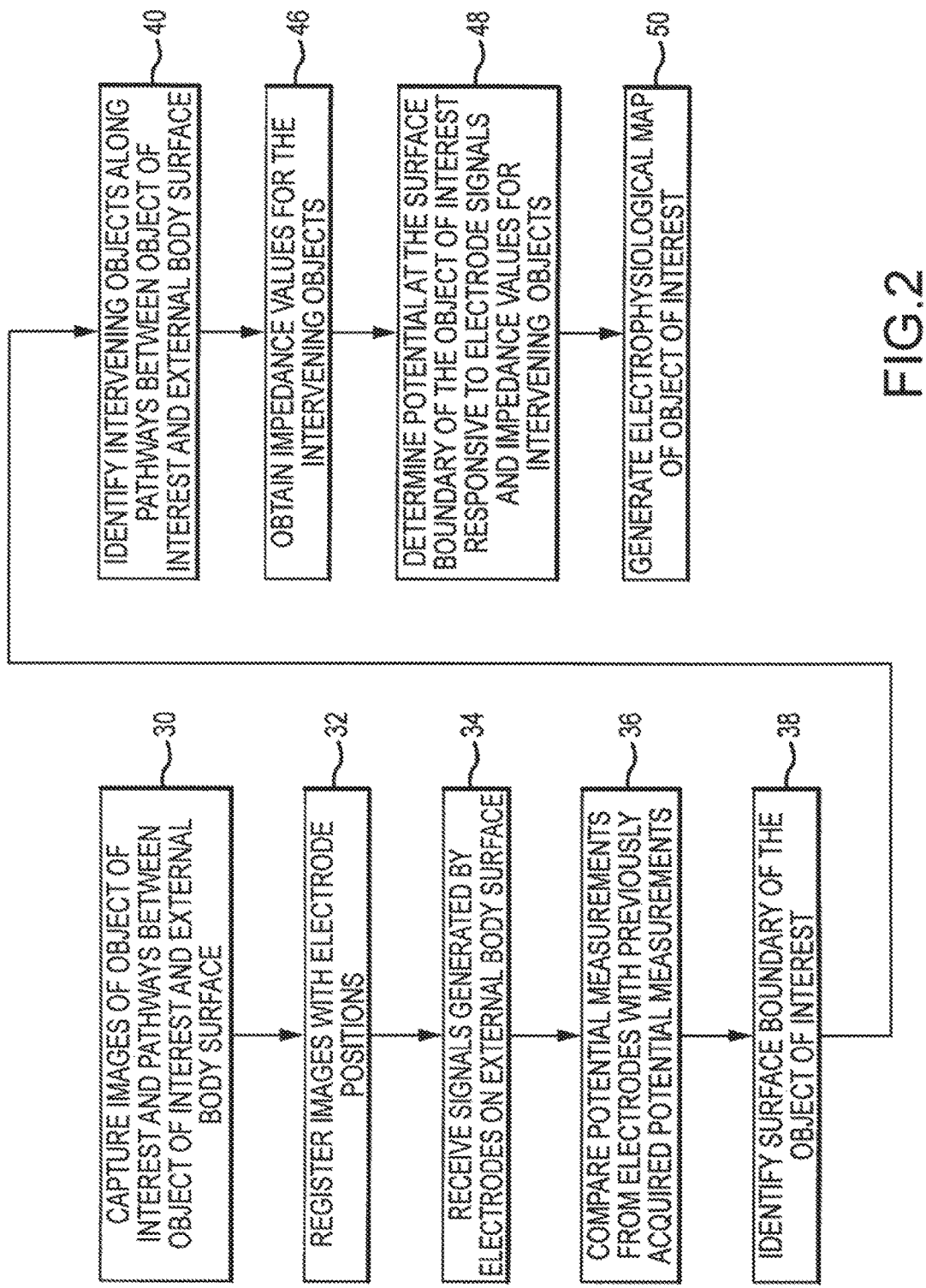
FIG. 2 is a flow chart diagram illustrating a method in accordance with one embodiment of the present teachings.

In accordance with one embodiment of the present invention, ECU 20 is configured with appropriate programming instructions or code (i.e., software) to perform several steps in a method for generating an electrophysiological map. Referring now to FIG. 2, the method may include the step 30 of capturing an image of an object of interest such as heart 12 and an image along a pathway between the object of interest and surface 24 of body 12. The images can include the positions on surface 24 at which electrodes 28 are located. While each of the images may be captured using a single imaging system 18, multiple imaging or modeling modalities or methods may be used for all or some of the images. The method may further include the step 32 of registering the images with the positions of electrodes 28. As noted hereinabove, to aid in registration fiducial markers may be placed on surface 24 of body 12 that correspond to the positions of electrodes 28 when housing 26 and/or electrodes 28 are placed on surface 24. For example, a housing or other structure having substantially similar dimensions to housing 26 and fiducial markers corresponding to one or more electrodes 28 may be placed on surface 24 of body 22 prior to imaging. Registration of the positions of the fiducial markers and electrodes 28 may be further assured by placing an ink marking on the body to permit consistent positioning of the markers and the electrodes 28. ECU 20 may use conventional algorithms to identify the fiducial markers and thereby register the images within the same coordinate system as electrodes 28.

The method may continue with the step 34 of receiving signals generated by one or more electrodes 28 disposed at positions on surface 24 of body 12. One or more electrodes 28 generate signals indicative of electric potentials measured at their respective positions on surface 24. These signals may be transmitted through conventional conductors and connectors to ECU 20 and may undergo signal processing (e.g., amplification, filtering, conversion) prior to receipt by ECU 20. The method may further include the step 36 of comparing the electric potential measured at each position by electrodes 28 to a previously acquired electric potential measured at the same position. In particular, initial electric potential measurements may be taken at each electrode 28 at the beginning of a procedure or at another time prior to or during the procedure to use as a baseline to correct later acquired measurements to account for changes in electric potential resulting from, for example, a change in salinity in body 22.

The method may continue with the step 38 of identifying a surface boundary of an object of interest such as heart 14 in body 12 using an image of the object of interest. ECU 20 may use conventional image processing algorithms including edge detection algorithms to identify the surface of the object of interest for which a measured impedance is desired.

Figure 3:
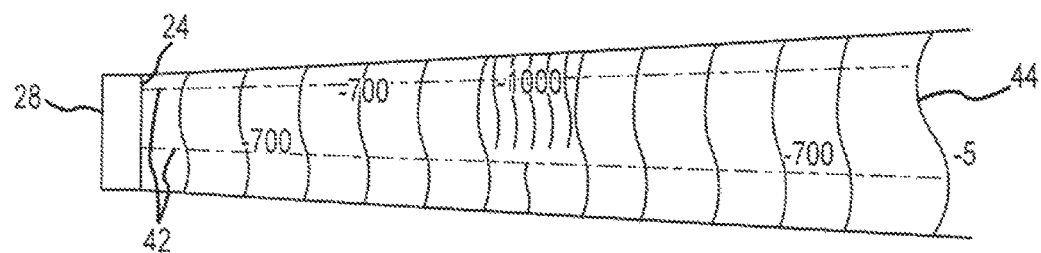
FIGS. 3 and 4 are representative drawings of an image showing intervening objects having varying tissue densities between a surface electrode and an object of interest in a body.
Figure 4:
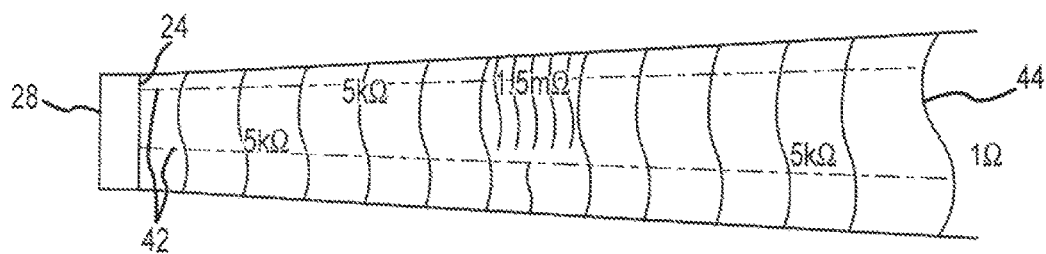

The method may further include the step 40 of identifying any intervening objects along pathways between the positions on surface 24 of body 12 at which electrodes 28 are located and the previously identified surface boundary of the object of interest from one or more images of the pathway. ECU 20 may identify appropriate images stored in a local or remote memory that, with reference to FIGS. 3-4, include portions of pathways 42 between the surface boundary 44 and the position of a given electrode 28 on surface 24 using, for example, the prior registration of the images. It should be understood that FIGS. 3-4 are intended to illustrate a small slice of a representative image. Using these images, ECU 20 is able to identify tissue densities at locations along the pathways 42 and tissue types. Referring to FIG. 3, different tissue densities have been illustrated by changes in width between the lines (to represent changes in grayscale as seen on a typical CT or MR image) as well as the inclusion of different CT or MR (Hounsfield) numbers. It should be understood, however, that the various densities and numbers are intended only to illustrate the invention and that an actual image would be much more complex and varied.

Different tissue types contribute different levels of impedance to the overall impedance between the body surface 24 and the surface boundary 44 of the object of interest and therefore have varying levels of impact on the electric potential measured at electrodes 28. Exemplary or average impedance values can be determined through testing including for example by direct measurement of tissues in animal studies and, subsequently, by comparing the measured values against measured values from actual studies and applying appropriate corrections. Referring again to FIG. 2, the method may therefore continue with the step 46 of obtaining impedance values for one or more of the intervening objects along the pathways 42 between the surface boundary 44 of the object of interest and the positions at which electrodes 28 are located. Referring to FIG. 4, the CT or MR numbers may be replaced with impedance values. Again, it should be understood that the values are exemplary only and intended solely to illustrate the invention. The values may be stored in a memory within a data structure, such as a conventional look up table, that correlates the intervening objects with impedance values. Step 46 may include the substep of accessing this data structure. Alternatively, ECU 20 may obtain impedance values for the intervening objects that are generated by an electrical impedance tomography system through its input/output interface. ECU 20 may obtain a total impedance value for the entire pathway between the body surface 24 and the surface boundary 44 of the object of interest or a sum of all of the intervening objects along the pathway 42 ("total impedance value"). However obtained, this value could then be stored in memory and used to correct electrogram signals received at each electrode 28.

The method may continue with the step 48 of determining an electric potential at the surface boundary of the object of interest responsive to the signal from the electrodes and the impedance values of the intervening objects along the pathways 42. Using the impedance values for the intervening objects, ECU 20 is able to filter out the contributions of these objects to the electric potential measured at electrode 28 to thereby obtain an electric potential at the surface boundary 44 of the object of interest. As mentioned above, total impedances measured along each of the pathways 42 between electrode 28 and boundary 44 can be summed to compute a total impedance value which can be used in the system to correct the signals read by the surface electrodes 28, e.g., by subtraction, addition, or by inclusion in an algorithm to correct the value read by the surface electrode 28 prior to the calculation of the electrograms on the surface of the object of interest, e.g., the heart or prior to the calculation of a map of the electrically activity on the surface of the object. In one embodiment of the invention where the object of interest is the heart 14, electric potentials at the epicardial surface may be obtained using the following formula from *Modeling and Imaging of Bioelectrical Activity* (Bin He, Ed.) (2004) p. 57:

$$\Phi_E(r) = -\frac{1}{4\pi}\int_{S_E}\frac{1}{r'_{EE}}\nabla'\Phi_E * n\, dS' + \qquad(Eq.\ 1)$$

$$\frac{1}{4\pi}\int_{S_E}\Phi_E\nabla'\left(\frac{1}{r'_{EE}}\right)*n\, dS' - \frac{1}{4\pi}\int_{S_B}\Phi_B\nabla'\left(\frac{1}{r'_{EB}}\right)*n\, dS'$$

where $\Phi_E$ and $\Phi_B$ are column matrices of epicardial and body surface potentials, $S_E$ and $S_B$ are the epicardial and body surfaces, $r'_{EE}$ is the scalar distance between the (observation) point of interest on the epicardial surface and another point on the epicardial surface, $r'_{BB}$ is the scalar distance between the (observation) point of interest on the epicardial surface and another point on the body surface 24, and n is a normal to the epicardial surface. The column matrices $\Phi_E$ and $\Phi_B$ may be determined using computational methods such as a boundary element method or a finite element method. In particular, ECU 20 may generate a mesh model or a volumetric model (made of cubes or tetrahedra) for each surface or volume, respectively, along a given pathway 42. The generated model would be based, at least in part, on the identification of the intervening objects (tissue types) along a given pathway 42 from images of the pathway 42 in step 40. Because the orientation of muscle fibers impacts impedance in muscle tissue, ECU 20 may further evaluate the orientation of the fibers from the images as part of the process in forming the models and obtaining the relevant impedance values. Once the model is generated, ECU 20 may then develop equations relating the impedance (or another variable) at each corner of the mesh or cube or tetrahedron to the impedance (or another variable) at other corners of the mesh or cube or tetrahedron. These equations are not limited to the boundary element method described in (Eq. 1), and may represent finite element method, finite volume method or other systems of equations known in the art. The column matrices $\Phi_E$ and $\Phi_B$ may be then be generated based on these equations. It should be understood that it is also possible to develop equations and matrices for each individual surface or volume in a similar manner and use the output of equations employing those matrices as an input to development of matrices for another surface or volume in a sequential manner. Once the matrices are generated, a generalized minimum residual (GMR) method may be employed as described in U.S. Pat. No. 7,016,719 to minimize errors when solving the above-identified equation (i.e. Eq. 1). It should be understood, however, that other methods known in the art may also be used to solve the above-identified equations.

The method may conclude with the step 50 of generating an electrophysiological map of the object of interest. ECU 20 may output a plurality of image or display signals to display 22 to generate the map.

Display 22 is provided to convey information to a clinician to assist in diagnosis and treatment. Display 22 may comprise a conventional computer monitor or other display device. Display 22 presents a graphical user interface (GUI) to the clinician. The GUI may include a variety of information including, for example, an image of the geometry of the object of interest, EP data associated with the object of interest, graphs illustrating voltage levels over time for various electrodes 28, and images of medical devices and related information indicative of the position of devices relative to the object of interest.

A system and method in accordance with the above-identified embodiments of the invention represents an improvement relative to conventional systems for generating electrophysiological maps because the inventive system and method results in more accurate electrophysiological maps of the heart and other internal body structures. By identifying different objects disposed between the object of interest and the surface of the body and accounting for the varying impedances created by these objects, the inventive system and method are able to more accurately measure electric potentials in the object of interest as opposed to conventional systems that rely on generalized mathematical models. The inventive system and method allow for adjustment of the electric potentials measured by the electrodes at the external body surface to account for the different objects and amounts of these objects along individual pathways and thereby generate a more accurate reading of the electrical activity in objects of interest such as the heart.

Although several embodiments of this invention have been described above with a certain degree of particularity, those skilled in the art could make numerous alterations to the disclosed embodiments without departing from the scope of this invention. All directional references (e.g., upper, lower, upward, downward, left, right, leftward, rightward, top, bottom, above, below, vertical, horizontal, clockwise and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not as limiting. Changes in detail or structure may be made without departing from the invention as defined in the appended claims.

What is claimed is:

1. A method for generating an electrophysiological map using an electronic control unit communicatively coupled to at least one electrode and an imaging apparatus, the method comprising:

receiving a signal generated by a first electrode of the at least one electrode, the first electrode disposed at a first position on an external surface of a body, said signal indicative of an electric potential measured at said first position;

generating an image of an object of interest identifying a surface boundary of the object of interest in said body using the image of the object of interest;

obtaining a first impedance value for a first intervening object along a first pathway between said first position on said external surface of said body and said surface boundary of sad object of interest;

determining a first electric potential at said surface boundary of said object of interest responsive to said signal from said first electrode and said first impedance value of said first intervening object along said first pathway; and generating an electrophysiology map of the body including the object of interest.

2. The method of claim 1, further comprising:
receiving a signal generated by a second electrode of the at least one electrode, the second electrode disposed at a second position on said external surface of said body, said signal indicative of an electric potential measured at said second position and said second electrode located at a known distance from said first electrode;
obtaining a second impedance value for a second intervening object along a second pathway between said second position on said external surface of said body and said surface boundary of sad object of interest; and
determining a second electrical potential at said surface boundary of said object of interest responsive to said signal from said second electrode and said second impedance value of said second intervening object along said second pathway.

3. The method of claim 1, further comprising identifying said first intervening object along said first pathway from one or more images of said first pathway.

4. The method of claim 3, further comprising capturing said image of said object of interest and said one of more images of said first pathway.

5. The method of claim 3, further comprising registering said one or more images of said first pathway with a position of said first electrode.

6. The method of claim 3, wherein said one or more images of said first pathway comprise computed tomography images or magnetic resonance images.

7. The method of claim 1, wherein obtaining the first impedance value comprises determining an orientation of a fiber of the first intervening object.

8. The method of claim 1, further comprising:
receiving a signal generated by a second electrode of the at least one electrode, the second electrode disposed at a second position on said external surface of said body, said signal indicative of an electric potential measured at said second position and said second electrode located at a known distance from said first electrode;
obtaining a second impedance value for a second intervening object along a second pathway between said second position on said external surface of said body and said surface boundary of sad object of interest;
determining a second electrical potential at said surface boundary of said object of interest responsive to said signal from said second electrode and said second impedance value of said second intervening object along said second pathway; and
averaging said first electrical potential and said second electrical potential at said surface boundary of said object of interest.

9. The method of claim 1, further comprising obtaining a second impedance value for a second intervening object along said first pathway, said first electric potential at said surface boundary of said object of interest determined responsive to said second impedance value.

10. The method of claim 1, further comprising:
obtaining a second impedance value for a second intervening object along said first pathway; and,
obtaining a total impedance value responsive to said first and second impedance values, said first electric potential at said surface boundary of said object of interest determined responsive to said total impedance value.

11. The method of claim 1, further comprising:
obtaining a second impedance value for a second intervening object along said first pathway; and,
obtaining an average value responsive to said first and second impedance values, said first electric potential at said surface boundary of said object of interest determined responsive to said average value.

12. The method of claim 1, further comprising comparing said first electric potential measured at said first position to a previously acquired electric potential measured at said first position.

13. The method of claim 1, wherein obtaining said first impedance value for said first intervening objects along said first pathway includes accessing a data structure in a memory, said data structure correlating said first intervening object with said first impedance value.

14. The method of claim 1, wherein determining said first electric potential at said surface boundary of said object of interest includes generating a model for a portion of said first pathway containing said first intervening object.

15. The method of claim 1, further comprising generating a model for a portion of said first pathway containing said first intervening object.

16. The method of claim 1, wherein the first impedance value is obtained by calculating the first impedance value from a tissue density of the first intervening object.

17. A method for generating an electrophysiological map using an electronic control unit communicatively coupled to at least one electrode and an imaging apparatus, comprising:
receiving a signal generated by a first electrode of the at least one electrode, the first electrode disposed at a first position on an external surface of a body, said signal indicative of an electric potential measured at said first position;
generating an image of an object of interest;
identifying a surface boundary of the object of interest in said body using one or more images of said object of interest;
identifying a first pathway between said first position on said external surface of said body and said surface boundary of sad object of interest;
identifying a first intervening object along said first pathway from one or more images of said first pathway;
obtaining a first impedance value for said first intervening object; and
determining a first electric potential at said surface boundary of said object of interest responsive to said signal from said first electrode and said first impedance value of said first intervening object along said first pathway; and
generating an electrophysiology map of the body including the body of interest.

18. The method of claim 17, wherein the first impedance value is obtained by calculating the first impedance value from a tissue density of the first intervening object.

19. The method of claim 17, further comprising generating a model for a portion of said first pathway containing said first intervening object.

20. The method of claim 17, further comprising registering said one or more images of said first pathway with a position of said first electrode.

* * * * *